United States Patent [19]

Tamm et al.

[11] Patent Number: 4,968,141
[45] Date of Patent: Nov. 6, 1990

[54] ELECTROTHERMAL ATOMIZATION FURNACE

[75] Inventors: Rolf Tamm, Am Fohrenbuhl; Gunther Rödel, Hinter den Garten, both of Fed. Rep. of Germany

[73] Assignee: The Perkin-Elmer Corporation, Norwalk, Conn.

[21] Appl. No.: 304,993

[22] Filed: Feb. 1, 1989

[30] Foreign Application Priority Data

Feb. 2, 1988 [DE] Fed. Rep. of Germany ....... 3802968

[51] Int. Cl.$^5$ ............................................ G01N 21/74
[52] U.S. Cl. ..................................... 356/312; 356/244
[58] Field of Search ................................ 356/312, 244

[56] References Cited

U.S. PATENT DOCUMENTS

| | | | |
|---|---|---|---|
| 3,862,805 | 1/1975 | Tamm et al. | 356/244 |
| 4,022,530 | 5/1977 | Braun et al. | 356/85 |
| 4,098,554 | 3/1974 | Huber et al. | 356/85 |
| 4,111,563 | 9/1978 | Tamm | 356/244 |
| 4,407,582 | 10/1983 | Woodriff | 356/312 |
| 4,432,643 | 2/1984 | Koizumi et al. | 356/312 |
| 4,726,678 | 2/1988 | Hutsch et al. | 356/244 |

Primary Examiner—F. L. Evans
Assistant Examiner—K. P. Hantis
Attorney, Agent, or Firm—Thomas Murphy; Edwin T. Grimes

[57] ABSTRACT

An electrothermal atomization furnace for atomizing samples for analysis by atomic absorption spectoscopy comprising a tubular furnace body (36) which is provided on both sides with longitudinal contact ribs (38, 40) and cylindrical contact pieces (18, 20) integral with these contact ribs. In one embodiment, bores (49, 50, 52, 54) are provided in the contact ribs (38, 40) parallel to the furnace body (36) in order to reduce the cross-section for the current supply along the center area of the furnace body (36). These bores are intersected by transverse bores (56, 58, 60 and 62, 64, 66, respectively) and communicate with inert gas passages (68, 70) so that the bores contribute to reduce the cross-section as well as to distribute the inert gas. In another embodiment, grooves are provided in the planar surfaces instead of the bores. An equal temperature distribution along the furnace body (36) is achieved. A hollow, generally semicylindrical inner body (76) with half of an internally threaded portion (78) is arranged in the furnace body (36).

21 Claims, 6 Drawing Sheets

ELECTROTHERMAL ATOMIZATION FURNACE

BACKGROUND AND SUMMARY OF THE INVENTION

The present invention relates generally to atomic absorption spectroscopy and more particularly to a furnace for electrothermal atomization of samples in atomic absorption spectroscopy.

Electrothermal atomizers, commonly referred to as heated graphite atomizers or graphite furnaces, are utilized in atomic absorption spectrophotometers for rendering the sample to be analyzed in atomic form. Typically, the furnaces comprise a tubular graphite member clamped between annular graphite contacts or electrodes engaging its respective ends. A radial aperture in the side wall of the tubular member at the midpoint of its length serves as a sample port accommodating the insertion of the substance to be analyzed into the tubular member.

The contacts, usually mounted in cooling jackets, are pressed into tight engagement with the ends of the tubular furnace member by resilient biasing means or a servomotor. An intense electrical current, passed longitudinally through the tubular member between the contacts heats the member to the high temperature required to convert the sample to a "cloud of atoms".

A measuring light beam of a line emitting light source which comprises the resonant spectral line of a looked-for element is passed through the annular graphite contacts and the longitudinal bore of the graphite tube. The amount of the looked-for element in the sample can be determined from the absorption of the measuring light beam.

In order to prevent rapid deterioration of the tubular graphite member by oxidation at the high temperatures required for atomization of the analyte, provision is made for enveloping it in a flow of inert protective gas. The graphite tube is surrounded by an inert gas such that oxygen does not get into contact with the graphite tube.

A non-uniform temperature distribution along the graphite tube results when the graphite tube is held at its ends. The graphite tube has a higher temperature in its central area than at the ends where the heat dissipates to the cooled contacts. This non-uniformity of temperature results in the deposition of sample on the cooler ends of the tubular member; the deposit is re-evaporated in subsequent use of the tubular member thereby contaminating the new sample.

A graphite furnace of the type just described is shown in Braun et al., U.S. Pat. No. 4,022,530 which is incorporated herein by reference. In this particular furnace, the contacts are tubular rather than annular. The two contacts extend around the graphite tube along its entire length between the contact surfaces except for a separating gap. An inert gas flow is passed into the graphite tube from both ends. This inert gas flow emerges through a radial bore of the graphite tube in its center. One of the tubular contacts has a radial bore which is aligned with the radial bore of the graphite tube.

In an attempt to achieve a more advantageous temperature distribution along the graphite tube, it has been proposed to pass the heating current transversely through the graphite tube rather than longitudinally. For this purpose, a contact arrangement is described in Woodriff, U.S. Pat. No. 4,407,582 wherein two pairs of interconnected contacts in the form of fork-shaped contact pieces are employed which engage the graphite tube radially on opposite sides. The heating current flows in a circumferential direction through the graphite tube in the area of the ends. The graphite tube is heated in the area of its ends and heat flows from the ends to the center to obtain a more uniform temperature distribution.

In this known contact arrangement, the electrodes engage the hot parts of the graphite tube; consequently, the reproducibility of the contact characteristics is poor. Furthermore, it is difficult to protect the graphite tube from exposure to atmospheric oxygen by means of an inert protective gas flow, resulting in short useful life of the graphite tube.

In Hutsch et al., U.S. Pat. No. 4,726,678 which is incorporated herein by reference and the publication in "Analytical Chemistry" 58 (1986), 1973, a graphite furnace is described in which the tubular furnace body has a rectangular cross-section and contact projections extend transversely to the axis of the furnace body. The furnace body and contact projections are formed as one integral graphite element. The contacting is provided in a cold area at planar contact surfaces.

In some embodiments of U.S. Pat. No. 4,726,678, the contact projections between the contact surfaces and furnace body have areas of a reduced cross-section. In one embodiment (FIG. 3), cutouts are provided which extend longitudinally to the furnace axis. These cutouts provide a reduction of the heat dissipation from the furnace body to the ends of the contact pieces and match electrical resistance to the output of the electrical power supply. In another embodiment (FIG. 4), it is stated that the contact projections are provided with multiple apertures and that this configuration is specifically suited for setting predetermined temperature profiles. Current is supplied at certain locations and flows through the furnace body in order to generate Joul's heat. This is similar to the arrangement of U.S. Pat. No. 4,407,582, except that the contacting is displaced to a cooler area.

In the known arrangement, the power is supplied along the tubular furnace body non-uniformly.

In German Pat. Application No. P 37 35 013.7, not pre-published, an electrothermal furnace is disclosed which comprises a tubular furnace body with contact projections provided on opposite sides and contact surfaces. The contact projections have longitudinal contact ribs and cylindrical contact projections with conical contact surfaces integral therewith. The contact ribs have contractions and are trapezoidal in plan view on the surface of the contact rib. The long parallel side of the trapezoid is adjacent to the furnace body while the contact projection is adjacent to the short parallel side of the respective trapezoid. The contact ribs have longitudinal cylindrical cutouts on both sides. The axes of the cutouts extend parallel to the axis of the furnace body in order to form the contractions. These cutouts however do not extend throughout the entire length of the contact ribs, but end at distance from a transverse center plane. In this manner, reinforcing ribs are formed in the center on both sides of the contact ribs. The reinforcing ribs extend along the transverse center plane perpendicular to the axis of the furnace and are connected to the contact ribs and the furnace body.

In German Pat. Application No. P 37 35 013.7, a platform for accommodation of samples is described which can be inserted into the furnace and which is heated only indirectly by the furnace. Contacts are provided between which the furnace is held and through which current is passed transversely through the furnace body. The contacts form a cavity into which inert gas is passed.

From German Pat. Application No. P 37 43 286.9, also not pre-published (corresponding to Tamm, U.S. Ser. No. 285,884 filed Dec. 16, 1988, commonly owned and incorporated herein by reference), an electrothermal furnace is disclosed which has a tubular furnace body with a lateral inlet port and a hollow, generally semicylindrical inner body. The inner body is arranged opposite the inlet port and is connected to the furnace body by one single web.

In Tamm et al., U.S. Pat. No. 3,862,805, a longitudinally heated graphite tube is disclosed wherein the inner wall has a plurality of annular cutouts or collars. There is also described a graphite tube in which the cutouts are arranged helically and virtually form a kind of a threaded portion.

In Tamm, U.S. Pat. No. 4,111,563, a longitudinally heated graphite tube is disclosed in which a tubular inner body made of graphite is held in a tubular outer body (furnace body) by radially extending ribs on opposite sides. The inner body is substantially shorter than the outer body and is arranged in the central area of the outer body.

It is an object of the present invention to overcome or mitigate the disadvantages of the prior art noted above and to provide a new and improved furnace for electrothermal atomization.

Another object of the invention is to provide an electrothermal atomization furnace which attains uniform temperature distribution along the tubular furnace body.

A further object is to provide such a furnace and contacting arrangement which facilitates effective protection of the furnace tube against exposure to atmospheric oxygen.

A further object of the invention is to provide such a furnace which is economical to manufacture.

Other objects will be in part obvious and in part pointed out in more detail hereinafter.

Accordingly, it has been found that the foregoing and related objects are attained in an electrothermal atomization furnace having a tubular electrothermal furnace body with a central portion and integral contact projections disposed on opposite sides of the furnace body. The contact projections have contact surfaces adapted for mounting engagement between cooperating current-supplying contacts or electrodes for passing a high electrical current through the furnace body. The contact projections define a cross-section between the contact surfaces and the furnace body with the contact projections containing bore means for reducing the cross section continuously along the central portion of the furnace body for uniform temperature distribution. In one embodiment, a plurality of bores in the contact projections extend parallel to the longitudinal axis of the furnace body to form the area of reduced cross section and are configured and disposed to produce uniform temperature distribution. In a further embodiment, a plurality of grooves are provided in the outer surface of the contact projections which extend parallel to the furnace axis to form the area of reduced cross-section continuously along the furnace body and are configured and disposed to produce a uniform temperature distribution. In both embodiments, the bores and grooves are fluidly connected to an inert gas passage for enveloping the furnace body in inert gas.

It has been found particularly advantageous that the areas of reduced cross-section extend continuously along the central part of the furnace body. In this regard, the design of the furnace according to the present invention is different from that of U.S. Pat. No. 4,726,678 where no continuous reduction of the cross-section is provided but rather discrete cutouts are provided in the contact projections, and is different from German Pat. Application No. P 37 35 013 where a reinforcing rib is formed just in the center and there reduces the electrical resistance for the supplied current.

DESCRIPTION OF THE PREFERRED EMBODIMENT

Figure 1:
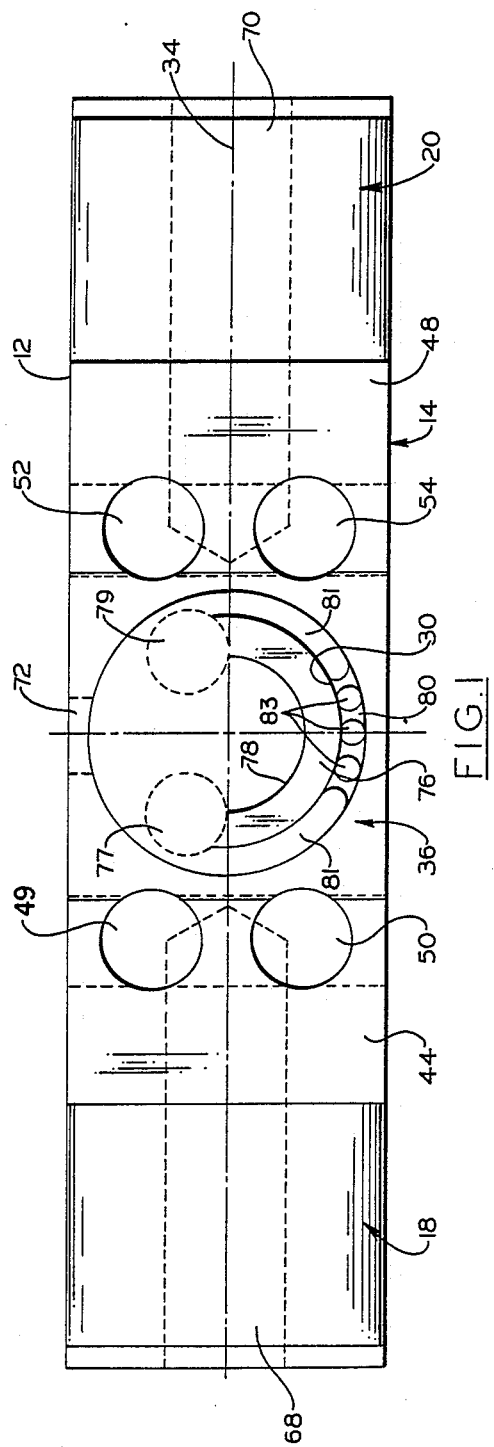
FIG. 1 is a front elevational view of the tubular furnace of the present invention with lateral contact projections, as viewed in the direction of the furnace axis.

Although specific forms of the present invention have been selected for illustration in the drawings, and the following description is drawn in specific terms for the purpose of describing these forms of the invention, the description is not intended to limit the scope of the invention which is defined in the appended claims.

Figure 3:
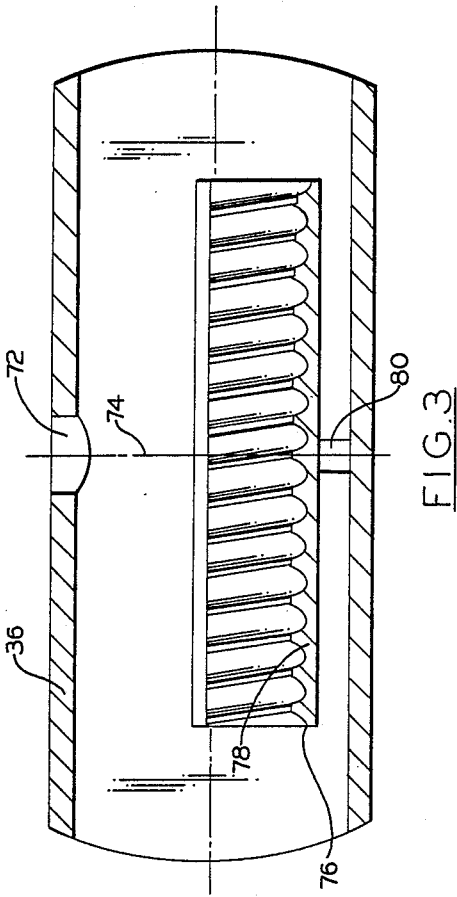
FIG. 3 is a longitudinal sectional view of the tubular furnace showing a hollow, generally semicylindrical inner body integral with the furnace.
Figure 2:
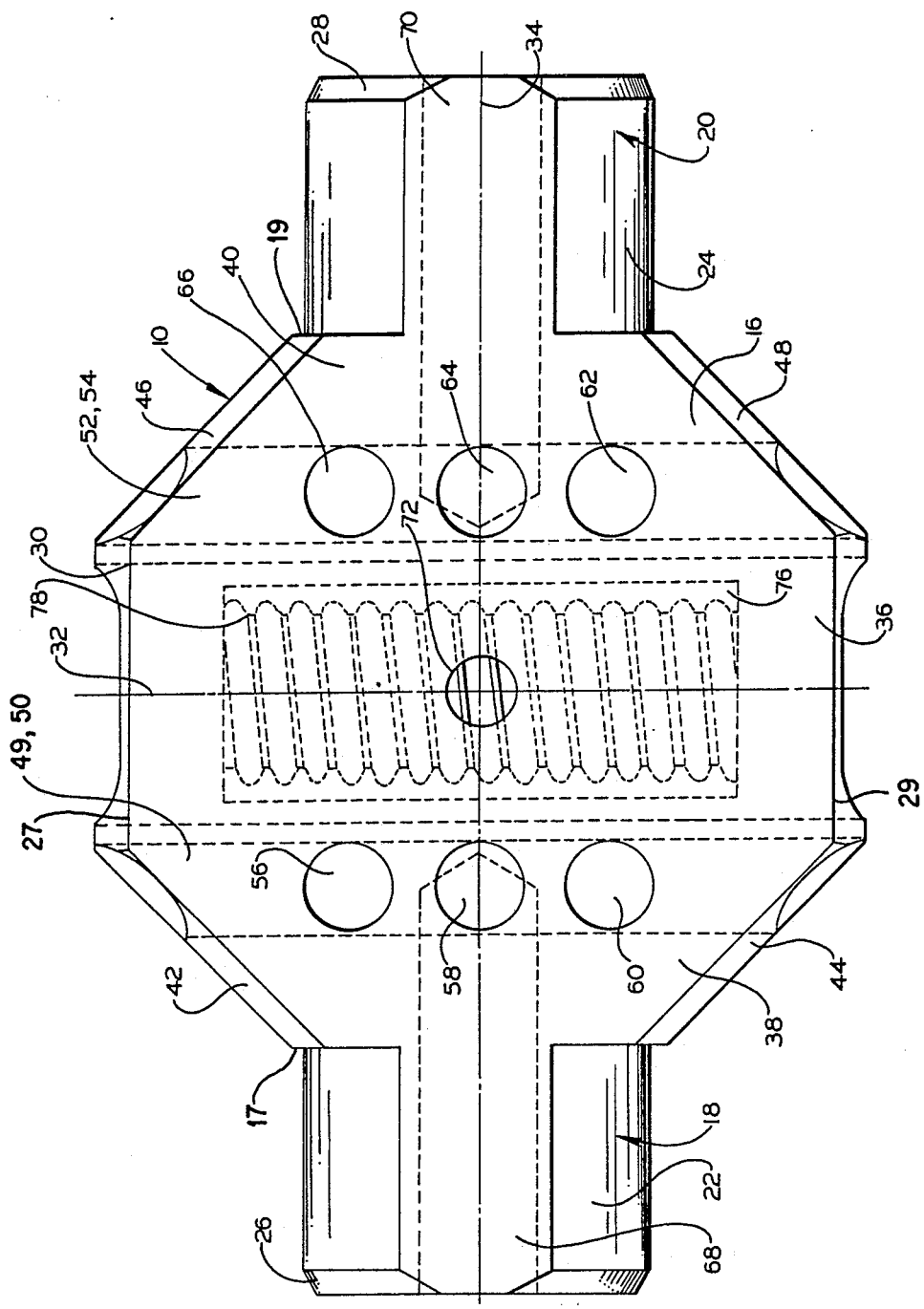
FIG. 2 is a plan view of the tubular furnace of FIG. 1.

Referring initially to FIGS. 1-3, the numeral 10 generally designates a graphite piece which has generally the shape of a plate with an upper planar surface 12 and a lower planar surface 14. The graphite piece 10 has a center portion 16 which has substantially the shape of a regular octagon in plan view. Projections are provided on two diametrically opposite sides 17, 19 of the octagon and form contact projections or pieces 18 and 20. These contact pieces 18 and 20 have cylindrical peripheral surfaces 22 and 24, respectively, which are limited by planar surfaces 12 and 14, respectively, on the top and bottom and are flattened thereby.

The contact pieces 18 and 20 are provided with conical contact surfaces 26 and 28, respectively. The furnace is held by these contact surfaces 26 and 28 between the current-supplying contacts or electrodes (not illustrated) of the furnace through which power is supplied for heating the furnace.

The sides 27, 29 of the octagon-shaped center portion 16 are perpendicular to the sides 17, 19 and are connected by a bore 30. The axis 32 of the bore 30 extends perpendicular to the axis 34 of the contact pieces 18, 20. The bore 30 forms the tubular furnace and the part of the center portion 16 between the sides 27, 29 forms a furnace body 36.

Contact ribs 38 and 40 are integral with the furnace body 36 on both sides and are trapezoidal in the plan view of FIG. 2. The contact ribs 38 and 40 are limited at their top and bottom by planar surfaces 12 and 14 and on their sides by inclined side faces 42, 44 and 46, 48, respectively. The long parallel side (unnumbered) of each trapezoid is adjacent to the furnace body 36. The short parallel sides of the trapezoids are the sides 17, 19 of the octagon and form the contact pieces 18 and 20, respectively. The contact ribs 38 and 40 have areas of a reduced cross-section.

In the embodiment of FIGS. 1-3, pairs of bores 49, 50 and 52, 54, respectively, are provided in the inclined side faces 42, 44 and 46, 48 in order to provide these areas of reduced cross-section. The bores 49, 50, 52 and 54 extend parallel to the axis 32 of the tubular furnace body 36 between the side faces 42, 44 or 46, 48, respectively, which means longitudinally to the entire furnace through the contact ribs. A reduction of the cross-section is achieved also along the central area of the furnace body 36.

Additionally, three transverse bores 56, 58, 60 and 62, 64, 66, respectively, are provided in the contact ribs 38 and 40 and extend between the planar surfaces 12 and 14. These transverse bores 56, 58, 60 and 62, 64, 66 intersect the bores 49, 50 and 52, 54, respectively. Inert gas passages 68 and 70, respectively, extend longitudinally to the axis 34 in the contact pieces 18 and 20. The inert gas passages 68 and 70 extend into the center portion 16 and intersect the bores 48, 50 and 52, 54, respectively, as can best be seen in FIG. 1. When inert gas from the contacts of the apparatus is supplied through the inert gas passages 68 and 70, such as described in German Pat. Application No. P 37 35 013.7, this inert gas is distributed through the bores 49, 50 and 52, 54, and through the transverse bores 56, 58, 60 and 62, 64, 66 and surrounds the furnace from all sides. Thereby, the access of air to the furnace and thus the burning of the furnace at the high atomizing temperatures is prevented. Accordingly, the bores accomplish the dual function of furnace protection and uniform temperature distribution.

A particularly uniform temperature distribution is achieved by reduction of the cross-section for the current supply in the central area of the furnace body.

The furnace body has an inlet port 72 through which the sample to be analyzed is introduced into the furnace. The axis 74 of the inlet port 72 is perpendicular to the axes 32, 34 of the furnace body 36 and the contact pieces 18, 20, respectively. The axis 74 of the inlet port 72 together with the axis 32 of the furnace body 36 define a longitudinal center plane. This is a plane perpendicular to the plane of the paper as viewed in FIG. 2 and along the axis 32.

Referring to FIG. 3, an inner body 76 of hollow, generally semicylindrical shape is located in the bore 30 of the furnace body 36. In the embodiment of FIG. 3, the inner surface of the inner body 76 has helical projections 78 which form virtually half of an internally threaded portion. These projections 78 impede the divergence of a liquid sample introduced through the inlet port 72 in the longitudinal direction of the inner body 76. Forming the projections 78 from part of an internally threaded portion has production benefits. First, the tubular furnace body can be threaded by a threading mechanism and the threading mechanism can be unscrewed. Subsequently, one half of the inner body can be bored out by two longitudinal bores 77, 79 as illustrated in broken line in FIG. 1.

The inner body 76 is held in the center of the furnace body only by a single web 80. Arcuated cutouts 81 are subsequently cut out of this web 80 between the inner body 76 and the furnace body 36 such that the remaining web 80 extends through an angle about the axis 32 of the furnace which is clearly smaller than 180°. The remaining web 80 is provided with bores 83 extending parallel to the axis 32 of the furnace so as to prevent current flow through the web 80 which could result in undesirable direct heating of the inner body 76 in the area of the web 80. Notably, it is a primary objective that the inner body 76 be heated only indirectly through the radiation of the inner wall of the furnace body 36 and such that the sample be atomized with a time delay so that the sample is not atomized before the inner wall of the furnace body is hot.

Figure 4:
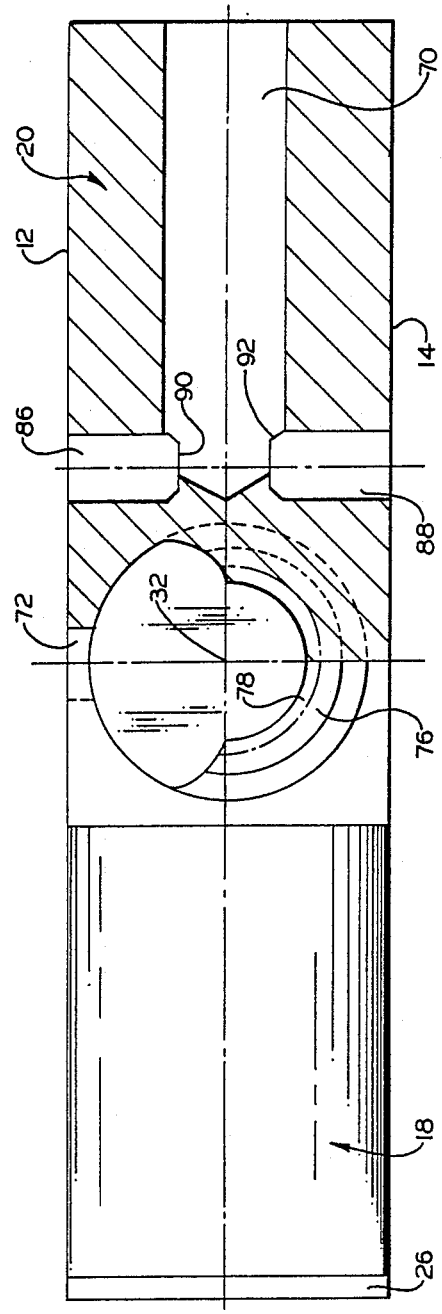
FIG. 4 is a view similar to FIG. 1, partially in section, of a further embodiment of the furnace of the present invention.
Figure 6:
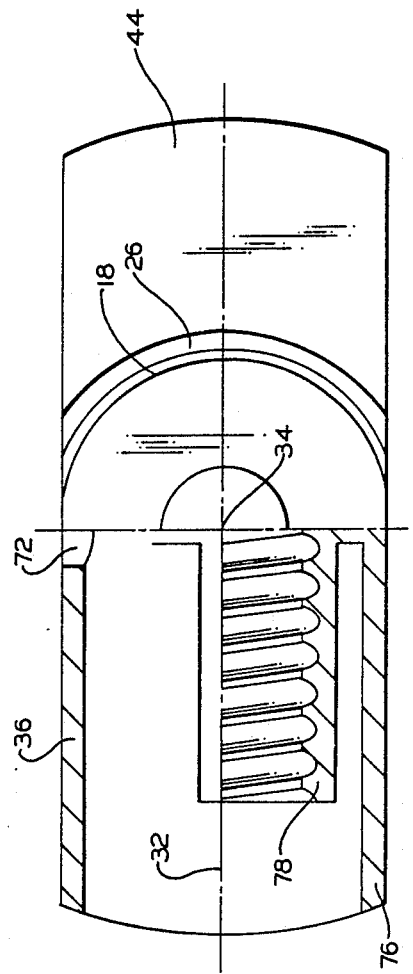
FIG. 6 is a lateral view of the furnace, as viewed from the right side in FIG. 4 and FIG. 5, partially in section.
Figure 5:
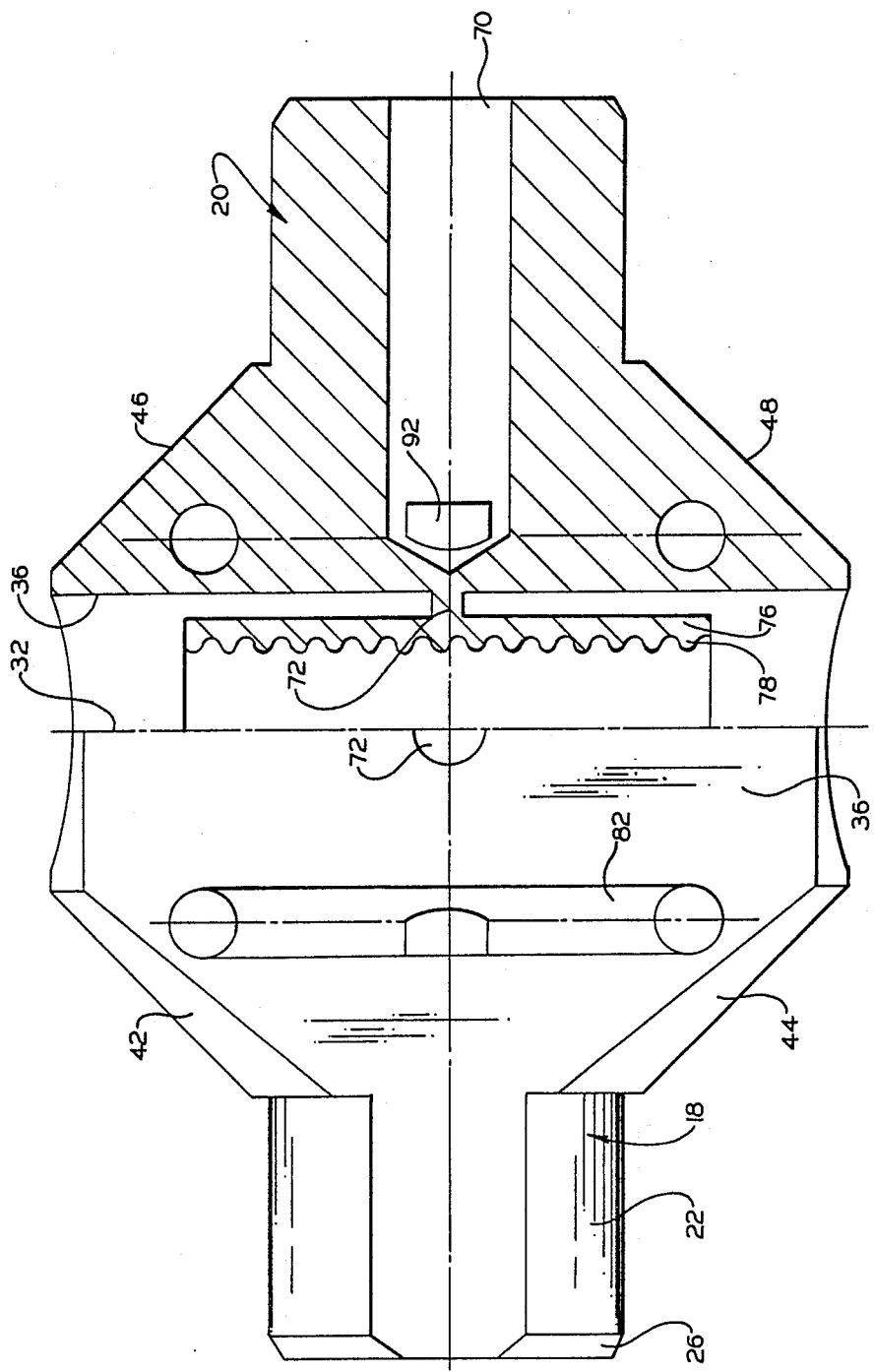
FIG. 5 is a plan view of the furnace of FIG. 4, similar to FIG. 2 and partially in section.

The furnace according to FIGS. 4-6 is constructed similarly to the furnace according to FIGS. 1-3. Accordingly, corresponding elements are designated by the same numerals and are not described in detail.

In the embodiment of FIGS. 4-6, the reduction of the cross-section for current supply along the center area of the furnace body 36 is achieved by cutouts or grooves 82 and 86, 88 in the planar surfaces 12 and 14. The cutouts are arranged parallel to the axis 32 of the furnace body 36 and terminate at a distance from the inclined side faces 42, 44 and 46, 48, respectively. Similar to the embodiment of FIGS. 1-3, the cutouts are dimensioned and disposed to reduce the cross-section for current supply along the central area of the furnace body so as to produce uniform temperature distribution along the furnace body.

As can be seen in FIG. 4, the cutouts, 86 and 88 for example, are intersected by the inert gas passages, such as 70. Thus, the inert gas flowing through the inert gas passages passes through the apertures 90 and 92 into the cutouts 86, 88 and emerges from these cutouts at both ends and along the entire furnace body 36.

The furnace described is mounted by means of the contact projections 18, 20 in the atomic absorption spectrometer between two current supplying contacts or electrodes. The measuring light beam of the atomic absorption spectrometer passes along the axis 32 of the furnace through the tubular furnace element 36 so as to extend above the inner body 76. A sample is supplied to the inner body 76 through the inlet port 72. The furnace is heated to high temperature by passing electrical current through the furnace The inner body 76 is heated mostly indirectly by radiation thereby atomizing the sample. A cloud of atoms is produced in which the elements of the sample, including the looked-for element, are present in atomic state. The amount of the looked-for element can be determined from the absorption of the measuring light beam originating from a line emitting light source. The contacts on the side of the instrument surround the furnace extensively. Inert gas is supplied through the contacts such that oxygen cannot get into contact with the furnace and the graphite furnace does not burn at high temperatures. The cutouts and/or bores previously described distribute this inert gas such that the furnace is surrounded entirely by the inert gas. The current supply is arranged transverse to the direction of the measuring light beam and to the axis of the furnace. Accordingly, an optimally uniform temperature distribution along the furnace is achieved by the furnace of the present invention as described.

Figure 7:
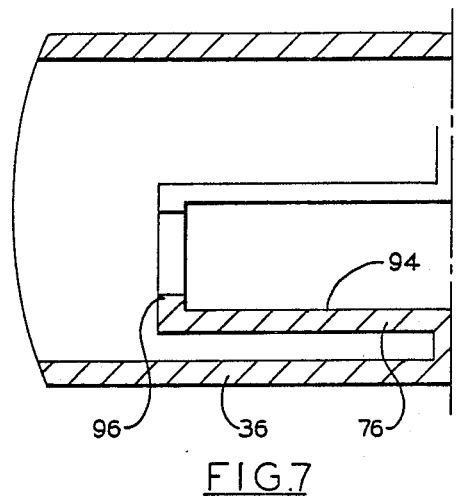
FIG. 7 shows a further embodiment of the furnace with a flat cylindrical inner surface in an illustration similar to FIG. 6.

In the embodiment of FIG. 7, a smooth-cylindrical inner surface 94 of the inner body 76 is provided instead of a helical inner surface. Internally projecting collars 96 are formed at the ends of the inner body 76. Such a design of the inner body 76 facilitates coating with pyrocarbon.

Figure 8:
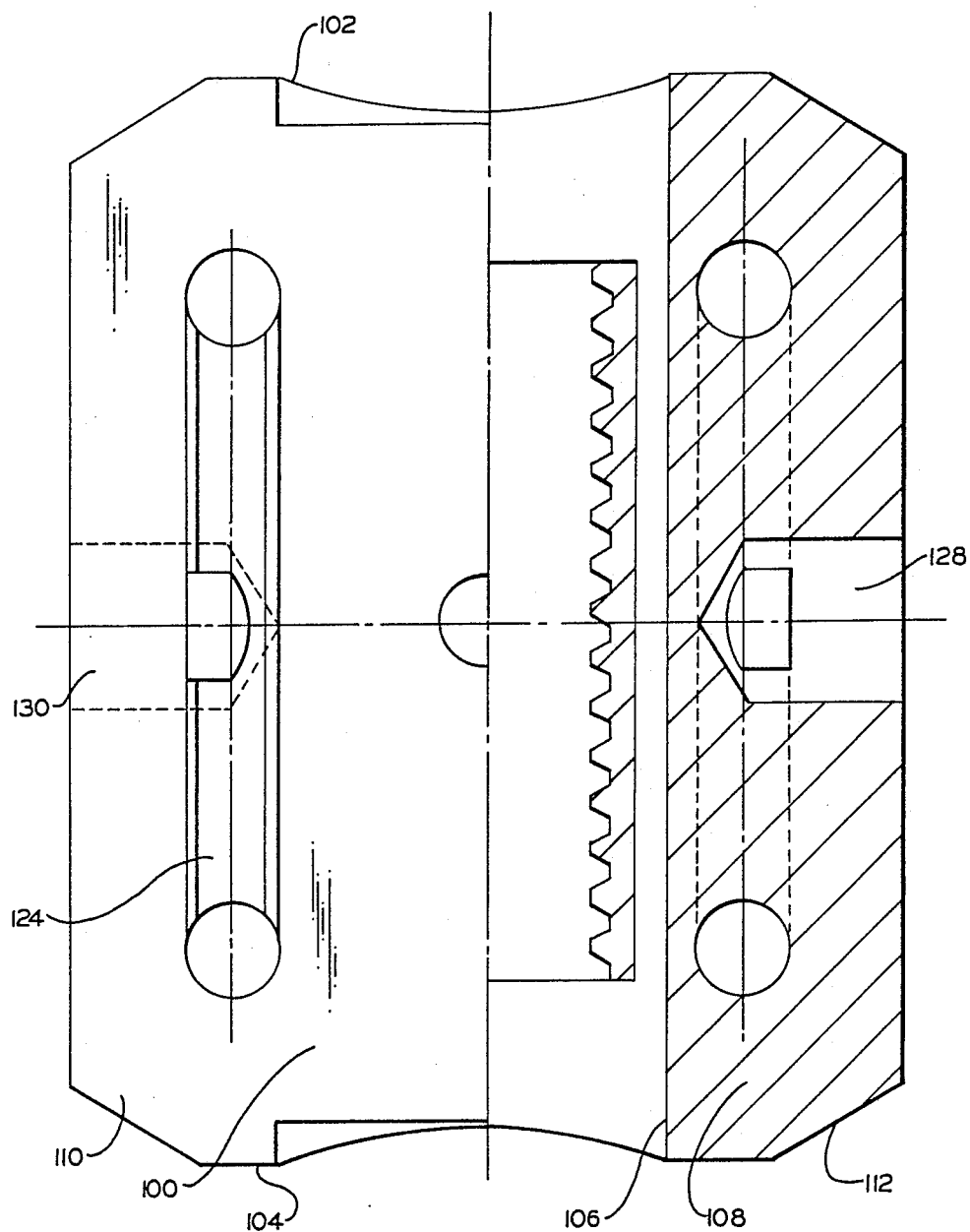
FIG. 8 shows a still further embodiment of the furnace of the present invention.
Figure 9:
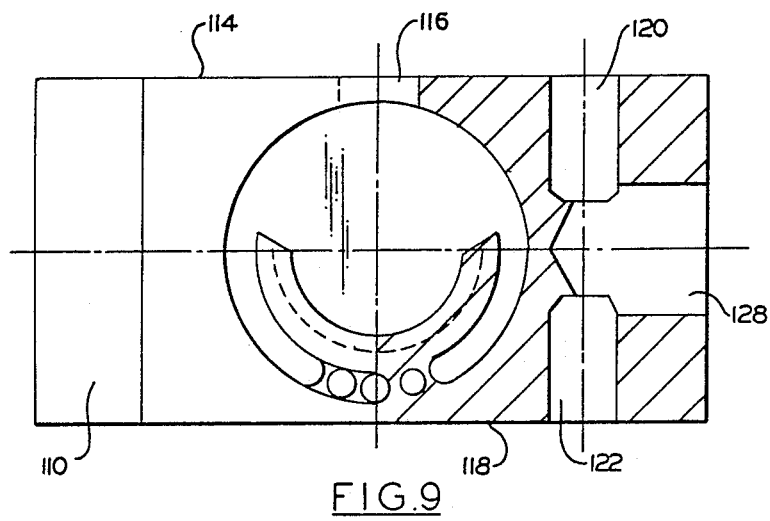
FIG. 9 is a sectional view taken perpendicularly to the furnace axis of the furnace body of FIG. 8.
Figure 10:
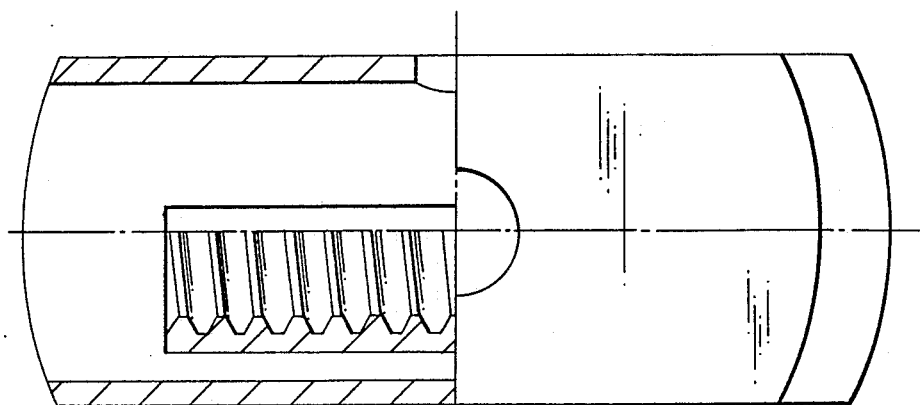
FIG. 10 is a longitudinal sectional view of the furnace of FIG. 8 and FIG. 9 taken along the furnace axis.

In the embodiment of FIGS. 8-10, a configuration is shown in which no cylindrical contact pieces are provided. The furnace is formed by a graphite body 100 having a generally cuboid shape. A bore 106 is provided in the graphite body between two end faces 102 and 104. The portion of the graphite body 100 between the end faces 102 and 104 with the bore 106 forms a furnace body 108. Two opposite longitudinal sides of the graphite body 100 are cut off conically and form conical contact surfaces 110 and 112 which engage the current supplying contacts on the side of the instrument. A bore 116 is provided as an inlet port in the upper surface 114 of the graphite body 100 of FIG. 9. The bore 116 opens into the bore 106. The axes of the bores 106 and 116 again define a longitudinal center plane. Grooves 120, 122 and 124, respectively, are provided in the upper surface 114 and the opposite bottom surface 118 (as viewed in FIG. 9) on both sides of the furnace 108. The grooves each extend throughout the center part of the furnace body 108. As can be seen in FIG. 9, the grooves 120, 122 are intersected by inert gas passages 128. The inner body 76 is held in the furnace in the same manner as in the embodiment of FIGS. 1-3 and need not be described in detail again.

As can be seen, several embodiments of the electrothermal atomizer furnace the present invention have been described, each of which provides optimum uniform temperature distribution and effective protection against atmospheric oxygen. Moreover, a furnace which is economical to manufacture is also provided.

As will be apparent to persons skilled in the art, various modifications and adaptations of the structure above described will become readily apparent without departure from the spirit and scope of the invention, the scope of which is defined in the appended claims.

What is claimed is:

1. An electrothermal atomization furnace assembly for atomizing sample for analysis by atomic absorption spectrophotometry comprising
   a tubular furnace member having a central portion,
   contact projections disposed on opposite sides of said furnace member,
   contact surfaces on said contact projections adapted for pressure mounting engagement between cooperating current-supplying contact surfaces for passing an electrical current through the furnace member,
   said contact projections defining a cross-sectional area between said contact surfaces and said furnace member,
   said contact projections containing void means for reducing said cross-sectional area, said void means being configured and disposed to provide a reduced cross-sectional area continuously along said central portion of said furnace member for uniform temperature distribution along said furnace member, and
   said contact projections further comprising an inert gas passageway adapted for connection to a source of inert gas, said inert gas passageway being connected to said void means such that inert gas can flow through said void means.

2. The device of claim 1 wherein said contact projections have upper and lower surfaces with said furnace member extending generally parallel between said surfaces, said furnace member has a longitudinal axis and said void means comprises a plurality of first grooves in said upper surface extending throughout the central portion of said furnace member and being generally parallel to said longitudinal axis, said first grooves being configured and disposed to provide a reduced cross-sectional area continuously along said central portion of said furnace member for uniform temperature distribution therealong.

3. The device of claim 2 wherein said void means further comprises a plurality of second grooves in said lower surface extending throughout the central portion of said furnace means and being generally parallel to said longitudinal axis, said second grooves being configured and disposed to combine with said first grooves to provide a reduced cross-sectional area continuously along said central portion of said furnace member for uniform temperature distribution therealong.

4. The device of claim 3 wherein said contact projections have opposing side faces and said first and second grooves terminate at a predetermined distance from said side faces.

5. The device of claim 3 wherein said contact projections further comprise a plurality of inert gas passages adapted for connection to a supply of inert gas, said first and second grooves being connected to said inert gas passages so that inert gas can flow through said inert gas passages and said grooves.

6. The device of claim 1 which comprises
   said furnace member having a lateral inlet port positioned in said central portion and a longitudinal axis, said axis and said inlet opening defining a longitudinal center plane of the furnace member,
   a hollow generally semicylindrical inner body disposed within said furnace member and integral therewith,
   said inner body being positioned symmetrically with respect to said longitudinal center plane opposite said inlet port and extending longitudinally throughout said central portion of said furnace member, and
   said inner body being integrally connected to said furnace member by a single web disposed opposite said inlet port.

7. The device of claim 6 wherein acurate cutouts are provided on opposite sides of said web between said inner body and said furnace member in the plane of said web such that said web extends about said longitudinal axis through an angular range substantially less than 180°.

8. The device of claim 7 wherein said web has a plurality of bores approximately parallel to said longitudinal axis.

9. The device of claim 6 wherein said inner body has an inner surface formed by helical ribs.

10. The device of claim 6 wherein said inner body has an inner surface which is smooth and cylindrically shaped and the ends of said inner body have internally projecting collars.

11. An electrothermal atomization furnace assembly for atomizing sample for analysis by atomic absorption spectrophotometry comprising:
a tubular furnace member having a central portion,
contact projections disposed on opposite sides of said furnace member,
contact surfaces on said contact projections adapted for pressure mounting engagement between cooperating current-supplying contact surfaces for passing an electrical current through the furnace member,
said contact projections defining a cross-sectional area between said contact surfaces and said furnace member,
said contact projections containing void means for reducing said cross-sectional area, said void means being configured and disposed to provide a reduced cross-sectional area continuously along said central portion of said furnace member for uniform temperature distribution along said furnace member, and
said contact projections further comprising a pair of contact ribs extending longitudinally on diametrically opposite sides of said furnace member, said contact ribs forming the area of reduced cross section, and each said contact projection projecting radially outwardly from said furnace member.

12. The device of claim 11 wherein said contact projections have a generally cylindrically shaped distal end portions.

13. The device of claim 11 wherein said furnace member has a longitudinal axis and said void means comprises a plurality of first bores in said contact ribs extending parallel to said axis to form the area of reduced cross section in said contact ribs, said first bores being configured and disposed for producing uniform temperature distribution along said furnace member.

14. The device of claim 13 wherein said contact ribs have upper and lower outer surfaces generally parallel to said furnace member and a plurality of second bores extend generally transverse to said first bores between said upper and lower surfaces.

15. The device of claim 14 wherein said contact projections further comprise a plurality of inert gas passages adapted for connection to a supply of inert gas, said inert gas passages being connected to said first bores and said first bores being connected to said second bores such that inert gas can flow through said inert gas passages and said first and second bores.

16. An electrothermal atomization furnace assembly for atomizing sample for analysis by atomic absorption spectrophotometry comprising
a tubular furnace member adapted for passing a light beam therethrough and having a central portion,
a pair of contact projections extending longitudinally on diametrically opposite sides of said furnace member and projecting outwardly therefrom,
said contact projections each having distal contact surfaces adapted for pressure mounting engagement between cooperating current-supplying electrodes for passing electrical current therethrough,
said contact projections having areas of reduced cross-section between said contact surfaces and said furnace member, and
said areas of reduced cross-section extending continuously along said central portion of said furnace member, said areas being dimensioned and configured to reduce the cross-section for current supply along the central portion of the furnace member so as to produce uniform heat distribution along said furnace member.

17. The device of claim 16 wherein said contact projections comprise bore means for producing uniform heat distribution along said furnace member, said bore means extending continuously along said central portion of said furnace member.

18. The device of claim 17 wherein said furnace member has a longitudinal axis and an inert gas passage adapted for connection to a supply of inert gas, and said bore means comprises a plurality of first bores in said contact projections extending generally parallel to said longitudinal axis, said first bores being dimensioned and configured for reducing the cross sectional area of said contact projections continually along said central portion so as to produce uniform heat distribution along said furnace member, said first bores being connected to said inert gas passage so that inert gas can flow through said first bores to surround said furnace member with inert gas.

19. The device of claim 18 wherein said bore means further comprises a plurality of second bores in said contact projections extending transverse to said first bores and interconnected to said first bores so that inert gas may flow therethrough.

20. The device of claim 17 wherein
said furnace member has top and bottom surfaces, a longitudinal axis and an inert gas passage adapted for connection to a supply of inert gas, and
said bore means comprises a plurality of first grooves in said top surface extending generally parallel to said longitudinal axis, said first grooves being dimensioned and configured for reducing the cross sectional area of said contact projections continually along said central portion for producing a uniform heat distribution along said furnace member, said first grooves being connected to said inert gas passage so that inert gas can flow through said first grooves to surround said furnace member with inert gas.

21. The device of claim 20 wherein said bore means comprises a plurality of second grooves in said bottom surface extending generally parallel to said longitudinal axis, said second grooves being dimensioned and configured for reducing the cross sectional area of said contact projections continually along said central portion for producing uniform heat distribution along said furnace member, said second grooves being connected to said inert gas passage so that inert gas can flow through said first and second grooves to surround said furnace member with inert gas.

* * * * *